Figure 1B:
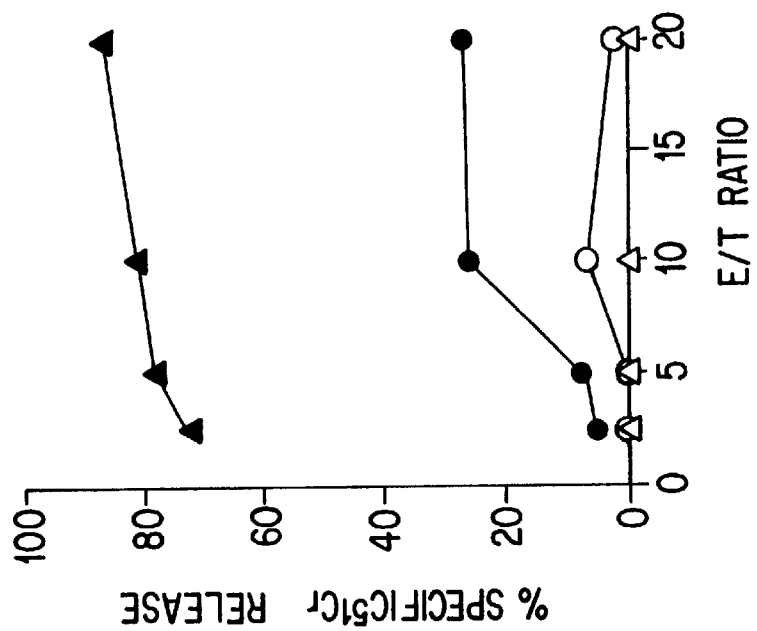

United States Patent [19]

Srivastava

[11] Patent Number: 5,985,270
[45] Date of Patent: Nov. 16, 1999

[54] ADOPTIVE IMMUNOTHERAPY USING MACROPHAGES SENSITIZED WITH HEAT SHOCK PROTEIN-EPITOPE COMPLEXES

[75] Inventor: Pramod K. Srivastava, Riverdale, N.Y.

[73] Assignee: Fordham University, New York, N.Y.

[21] Appl. No.: 08/527,546

[22] Filed: Sep. 13, 1995

[51] Int. Cl.[6] .................. A01N 63/00; A61K 39/385; A61K 45/05; C07K 14/435
[52] U.S. Cl. .................... 424/93.71; 424/193.1; 424/277.1; 424/184.1; 424/85.7; 424/85.1; 424/85.2; 424/85.5; 424/85.6; 530/350; 530/351; 514/2
[58] Field of Search .................... 424/184.1, 193.1, 424/85.1, 85.2, 85.5, 85.6, 85.7, 93.71, 277.1; 514/2; 530/350, 351

[56] References Cited

U.S. PATENT DOCUMENTS

| | | |
|---|---|---|
| 4,690,915 | 9/1987 | Rosenberg . |
| 5,188,964 | 2/1993 | McGuire et al. . |
| 5,232,833 | 8/1993 | Sanders et al. . |
| 5,348,945 | 9/1994 | Berberian et al. . |

FOREIGN PATENT DOCUMENTS

| | | |
|---|---|---|
| 195 02 985 A1 | 7/1997 | Germany . |
| 2 251 186 | 7/1992 | United Kingdom . |
| WO 89/12455 | 12/1989 | WIPO . |
| WO 90/02564 | 3/1990 | WIPO . |
| WO 91/15572 | 10/1991 | WIPO . |
| WO 92/01717 | 2/1992 | WIPO . |
| WO 92/08484 | 5/1992 | WIPO . |
| WO 92/08488 | 5/1992 | WIPO . |
| WO 93/14118 | 7/1993 | WIPO . |
| WO 93/17712 | 9/1993 | WIPO . |
| WO 93/18146 | 9/1993 | WIPO . |
| WO 93/18147 | 9/1993 | WIPO . |
| WO 93/18150 | 9/1993 | WIPO . |
| WO 93/21529 | 10/1993 | WIPO . |
| WO 93/24136 | 12/1993 | WIPO . |
| WO 94/02156 | 2/1994 | WIPO . |
| WO 94/03208 | 2/1994 | WIPO . |
| WO 94/04676 | 3/1994 | WIPO . |
| WO 94/11513 | 5/1994 | WIPO . |
| WO 94/29459 | 12/1994 | WIPO . |
| WO 95/24923 | 9/1995 | WIPO . |
| WO 96/10411 | 4/1996 | WIPO . |
| WO 97/06685 | 2/1997 | WIPO . |
| WO 97/06821 | 2/1997 | WIPO . |
| WO 97/06828 | 2/1997 | WIPO . |
| WO 97/26910 | 7/1997 | WIPO . |

OTHER PUBLICATIONS

Barrios et al., 1994, "Specificity of antibodies induced after immunization of mice with the mycobacterial heat shock protein of 65kD", Clin. Exp. Immunol., 98:224–228.
Barrios et al., 1994, "Heat shock protein as carrier molecules: in vivo helper effect mediated by *Escherichia coli* GroEl and DnaK proteins requires cross–linking with antigen", Clin. Exp. Immunol., 98:229–233.
Barrios et al. (1992) "Mycobacterial heat–shock proteins as carrier molecules. II: The use of the 70–kDa mycobacterial heat–shock protein as carrier for conjugated vaccines that can circumvent the need for adjuvants and Bacillus Calmette Guérin priming", *Eur. J. Immunol.* 22:1365–1372.
Basombrío (1970) "Search for common antigenicities among twenty–five sarcomas induced by methylcholanthrene", *The Institute for Cancer Research* 30:2458–2462.
Blachere et al. (1993) "Heat Shock Protein Vaccines Against Cancer," *Journal of Immunotherapy* 14:352–356.
Blachere and Srivastava (1993) "Immunization with GP96 heat shock proteins isolated from tumors or influenza virus infected cells elicits MHC–restricted, antigen–specific cytotoxic T lymphocytes against the corresponding cells", *J. Cellular Biochem. Keystone Symposia* NZ502, p. 124.
Boon "Toward a genetic analysis of tumor rejection antigens", *Advances in Cancer Research* 58:177–210.
Craig (1993) "Chaperones: Helpers Along the Pathways to Protein Folding", *Science* 260:1902–1904.
Elliott et al. (1990) "Naturally Processed Peptides", *Nature* 348:195–197.
Falk et al. (1991) "Allele–specific Motifs Revealed by Sequencing of Self–peptides Eluted from MHC Molecules", *Nature* 351:290–296.
Falk et al. (1990) "Cellular Peptide Composition Governed by Major Histocompatibility Complex Class I Molecules", *Nature* 348:248–251.
Fedweg and Srivastava "Evidence for biochemical heterogeneity of gp96 heat shock protein/tumor rejection antigen", *Mount Sinai School of Medicine* NZ 206, p. 108.
Flynn et al. (1989) "Peptide binding and release by proteins implicated as catalysts of protein assembly", *Science* 245:385–390.
Flynn et al. (1991) "Peptide–binding Specificity of the Molecular Chaperone BiP", *Nature* 353:726–730.
Franklin (1993) "Making vaccines fit the cancer", *New Scientist* 140:17.
Gething et al. (1992) "Protein Folding in the Cell", *Nature* 355:33–45.
Globerson and Feldman (1964) "Antigenic specificity of benzo[a]pyrene–induced sarcomas", *Journal of the National Cancer Institute* 32(6):1229–1242.

(List continued on next page.)

Primary Examiner—Lila Feisee
Assistant Examiner—Geetha P. Bansal
Attorney, Agent, or Firm—Pennie & Edmonds LLP

[57] ABSTRACT

The present invention relates to methods and compositions for enhancing immunological responses and for the prevention and treatment of infectious diseases or primary and metastatic neoplastic diseases based on the administration of macrophages and/or other antigen presenting cells (APC) sensitized with heat shock proteins non-covalently bound to peptide complexes and/or antigenic components. APC are incubated in the presence of hsp-peptide complexes and/or antigenic components in vitro. The sensitized cells are reinfused into the patient with or without treatment with cytokines including but not limited to interferon-α, interferon-α, interleukin-2, interleukin-4, interleukin-6 and tumor neurosis factor.

29 Claims, 3 Drawing Sheets

OTHER PUBLICATIONS

Jakob et al. (1993) "Small Heat Shock Proteins Are Molecular Chaperones", *J. Biol. Chem.* 268:1517–1520.

Jardetzky et al. (1991) "Identification of Self Peptides Bound to Purified HLA–B27", *Nature* 353:326–329.

Lakey et al (1987) "Identification of a peptide binding protein that plays a role in antigen presentation", *Proc. Natl. Acad. Sci. USA* 84:1659–1663.

Lanzavecchia (1993) "Identifying Strategies for Immune Intervention", *Science* 260:937–944.

Lévy (1991) "ATP is Required for In Vitro Assembly of MHC Class I Antigens but Not for Transfer of Peptides across the ER Membrane", *Cell* 67:265–274.

Li and Srivastava (1993) "Tumor rejection antigen gp96/grp94 is an ATPase: Implications for protein folding and antigen presentation", *EMBO J.* 12(8):3143–3151.

Lindquist and Craig (1988) "The heat–shock proteins", *Ann. Rev. Genet.* 22:631–677.

Luescher et al. (1991) "Specific Binding of Antigenic Peptides to Cell–associated MHC Clas I Molecules", *Nature* 351:72–77.

Lukacs et al. (1993) "Tumor cells transfected with a bacterial heat–shock gene lose tumorigenicity and induce protection against tumor", *J. Exp. Med.* 178:343–348.

Lussow et al. (1991) "Mycobacterial heat–shock proteins as carrier molecules", *Eur. J. Immunol.* 21:2297–2302.

Madden et al. (1991) "The Structure of HLA–B27 Reveals Nonamer Self–peptides Bound in an Extended Conformation", *Nature* 353:321–325.

Maki et al. (1993) "Mapping of the Genes for Human Endoplasmic Reticular Heat Shock Protein gp96/grp94", *Somatic Cell Mol. Genetics* 19(1):73–81.

Maki et al. (1990) "Human homologue of murine tumor rejection antigen gp96: 5'–Regulatory and coding regions and relationship to stress–induced proteins", *Proc. Natl. Acad. Sci. USA* 87:5658–5663.

McCall et al. (1989) "Biotherapy: A New Dimension in Cancer Treatment", *Biotechnology* 7:231–240.

Nelson et al. (1992) "The Translation Machinery and 70 kd Heat Shock Protein Cooperate in Protein Synthesis", *Cell* 71:97–105.

Palladino et al. (1987) "Expression of shared tumor–specific antigen by two chemically induced BALB/c sarcomas", *Cancer Research* 47:5074–5079.

Prehn and Main (1957) "Immunity to methylcholanthrene–induced sarcomas", *Journal of the National Cancer Institute* 18(6):769–778.

Rosenberg et al. (1988) "Use of Tumor Infiltrating Lymphocytes and Interleukin–2 in the Immunotherapy of Patients with Metastatic Melanoma", *New England J. Med.* 319:1676–1680.

Rothman (1989) "Polypeptide Chain Binding Proteins: Catalysts of Protein Folding and Related Processes in Cells", *Cell* 59:591–601.

Rötzschke et al. (1990) "Isolation and Analysis of Naturally Processed Viral Peptides as Recognized by Cytotoxic T cells", *Nature* 348:248–251.

Schumacher et al. (1991) "Peptide Selection by MHC Class I Molecules", *Nature* 350:703–706.

Srivastava et al. (1991) "Protein Tumor Antigens", *Curr. Opin. Immunol.* 3:654–658.

Srivastava et al. (1984) "The Serologically Unique Cell Surface Antigen of Zajdela Ascitic Hepatoma is also its Tumor–Associated Transplantation Antigen", *Int. J. Cancer* 33:417–422.

Srivastava et al. (1989) "Identification of a Human Homologue of the Murine Tumor Rejection Antigen GP96," *Cancer Res.* 49:1341–1343.

Srivastava et al. (1988) "Individually Distinct Transplantation Antigens of Chemically Induced Mouse", *Immunology Today* 9:78–83.

Srivastava et al. (1988) "Chromosonal Assignment of the Gene Encoding the Mouse Tumor Rejection Antigen gp96", *Immunogenetics* 28:205–207.

Srivastava et al. (1987) "5'–Structural analysis of genes encoding polymorphic antigens of chemically induced tumors", *Proc. Natl. Acad. Sci. USA* 84:3807–3811.

Srivastva et al. (1993) "Peptide–Binding Heat Shock Proteins in the Endoplasmic Reticulum: Role in Immune Response to Cancer and in Antigen Presentation", *Advances in Cancer Research* 62:153–177.

Srivastava and Maki (1991) "Stress–induced proteins in immune response cancer", *Microbiol. Immunol.* 167:109–123.

Srivastava and Heike (1986) "Tumor–specific immunogenicity of stress–induced proteins: Convergence of two evolutionary pathways of antigen presentation?", *Seminars in Immunology* 3:57–64.

Srivastava et al. (1986) "Tumor rejection antigens of chemically induced sarcomas of inbred mice", *Proc. Natl. Acad. Sci. USA* 83:3407–3411.

Szikora et al. (1990) "Structure of the gene of tum–transplantation antigen P35B presence of a point mutation in the antigenic allele", *EMBO J.* 9(4):1041–1050.

Topallian et al. (1989) "Tumor Specific Cytolysis by Lymphocytes Infiltrating Human Melanomas", *J. Immunol.* 142:3714–3725.

Udono (1993) "Heat shock proteins HSP70, HSP90 and GP96 elicit tumor specific immunity to the tumors from which they are isolated", *J. Cell. Biochem.* Suppl. 17D:113 (Abstract NZ225).

Udono et al. (1993) "Heat Shock Protein 70–associated Peptides Elicit Specific Cancer Immunity", *J. Exp. Med.* 178:1391–1396.

Ullrich et al. (1986) "A mouse tumor–specific transplantation antigen is a heat shock–related protein", *Proc. Natl. Acad. Sci. USA* 83:3121–3125.

Vanbuskirk et al. (1989) "Peptide binding protein having a role in antigen presentation is a member of the hsp70 heat shock family", *J. Exp. Med.* 170:1799–1809.

Welch et al. (1985) "Rapid Purification of Mammalian 70,000–Dalton Stress Proteins: Affinity of the Proteins for Nucleotides", *Mol. Cell. Biol.* 5:1229–1237.

Welch (1993) "How Cells Respond to Stress", *Scientific American* pp. 56–64.

Young (1990) "Stress Proteins and Immunology", *Annu. Rev. Immunol.* 8:401–420.

Yu et al. (1991) "Sequence Analysis of Peptides Bound to MHC Class II Molecules", *Nature* 353:622–627.

Martin et al., (1986) "Role of Murine Tumor Models in Cancer Treatment Research", *Cancer Research* 46:2189–2192.

Nieland et al., (1996) "Isolation of an immunodominant viral peptide that is endogenously bound to the stress protein GP96/GRP94", Proc. Natl. Acad. Sci. USA 93:6135–6139.

Suto et al., (1995) "A Mechanism for the Specific Immunogenicity of Heat Shock Protein–Chaperoned Peptides", Science 269:1585–1588.

Udono et al., (1994) "Comparison of Tumor–Specific Immunogenicities of Stress–Induced Proteins gp96, hsp90, and hsp70", J. Immunol. 152:5398–5403.

Bartholeyns and Lopez, 1994, "Immune control of neoplasia transfer of macrophages: potentiality for antigen presentation and gene transfer", Anticancer Research 14:2673–2676.

Chou et al., 1988, "Adoptive immunotherapy of microscopic and advanced visceral metastases with in vitro sensitized lymphoid cells from mice bearing progressive tumors", J. Immunology 141:1775–1781.

Grabbe et al., 1991, "Tumor antigen presentation by mature epidermal cells", J. Immunology 146:3656–3661.

Ramsey and Rank, 1991, "Resolution of chlamydial genital infection with antigen–specific T–lymphocyte lines", Infection and Immunity 59:925–931.

Suyu et al., 1989, "Lymphocytes generated by in vivo priming and in vitro sensitization demonstrate therapeutic efficacy against a murine tumor that lacks apparent immunogenicity", J. Immunology 143:740–748.

Blachere et al. (Mar. 1993) "Immunization with GP96 heat shock proteins isolated from tumors or influenza virus infected cells elicits MHC–restricted, antigen–specific cytotoxic T lymphocytes against the corresponding cells/antigens", J Cell Biochem Suppl 17D:124 (Abstract NZ 502).

Mulé et al. (1984) "Adoptive Immunotherapy of Estalished Pulmonary Metastases with LAK Cells and Recombinant Interleukin–2", Science 225:1487–1489.

Srivastava et al. (Mar. 1993) "Evidence for peptide–chaperoning by the endoplasmic reticular heat shock protein GP96: Implications for vaccination against cancer and infectious diseases", J Cell Biochem Suppl 17D:94 (Abstract NZ014).

Thomas et al. (1982) "Molecular and Cellular Effects of Heat Shock and Related Treatments of Mammalian Tissue–Culture Cells", Cold Spring Harbor Symp Quant Biol 46:985–996.

Levinson et al. (1979) "Metal Binding Drugs Induce Synthesis of Four Proteins in Normal Cells", Biol Trace Element Research 1:15–23.

Aldovini et al. (1992) "The New Vaccines", *Technology Review* pp. 24–31.

Cohen (1993) "Cancer Vaccines Get A Shot In The Arm", *Science* 262:841–843.

Melnick (1985) "Virus Vaccines: An Overview", Proceedings of the First Annual Southwest Foundation for Biomedical Research International Symposium, Houston, Texas, Nov. 8–10, 1984, *American Society for Microbiology* pp. 1–13.

Salk et al. (1993) "A Strategy for Prophylactic Vaccination Against HIV", *Science* 260:1270–1272.

Subbarao et al. (1992) "A General Overview of Viral Vaccine Development," *Genetically Engineered Vaccines* 327:51–57.

Welch et al. (1982), "Purification of the Major Mammalian Heat Shock Proteins", *J. Biol. Chem.* 257:14949–14959.

Oldharn, RK, (1987) Immunotherapy: Old Concepts and New Approaches. In: Klipper & Machor, eds: Present Status of Non Toxic Concepts in Cancer., Karefr, Basll, pp. 1–21.

Grable et al J. Immunol 146:3656–61 (1991).

Melief & Kast (1992) Lessons from T cell Responces to virus induced tumours for cancer eradication in general. In: A New Look at Tumor Immunology McMichael & Bodner (eds), Cold Spr. Harbor Lab. Press. pp. 81–99.

ADOPTIVE IMMUNOTHERAPY USING MACROPHAGES SENSITIZED WITH HEAT SHOCK PROTEIN-EPITOPE COMPLEXES

This invention was made with government support under grant number CA44786 awarded by the National Institutes of Health. The government has certain rights in the invention.

1. INTRODUCTION

The present invention relates to compositions and methods of adoptive immunotherapy for the prevention and/or treatment of primary and metastatic cancer and other immunological or infectious disorders in humans using macrophages sensitized with non-covalent complexes of heat shock protein (hsp) and antigenic molecules. In the practice of the adoptive immunotherapy as a method of the invention, compositions of hsp including, but not limited to, hsp70, hsp90, gp96 alone or in combination with each other, non-covalently bound to antigenic molecules, are used to sensitize macrophages in vitro to augment immune responses to tumors and infectious agents in vivo, upon infusion into the patient. In the practice of the prevention and treatment methods against infectious diseases and cancer, complexes of antigenic molecules and heat shock/stress proteins (hsps) including, but not limited to, hsp70, hsp90, gp96 alone or in combination with each other, are used to augment the immune response to genotoxic and nongenotoxic factors, tumors and infection.

2. BACKGROUND OF THE INVENTION

Adoptive immunotherapy of cancer refers to a therapeutic approach in which immune cells with an antitumor reactivity are administered to a tumor-bearing host, with the aim that the cells mediate either directly or indirectly, the regression of an established tumor. Transfusion of lymphocytes, particularly T lymphocytes, falls into this category and investigators at the National Cancer Institute (NCI) have used autologous reinfusion of peripheral blood lymphocytes or tumor-infiltrating lymphocytes (TIL), T cell cultures from biopsies of subcutaneous lymph nodules, to treat several human cancers (Rosenberg, S. A., U.S. Pat. No. 4,690,914, issued Sep. 1, 1987; Rosenberg, S. A., et al., 1988, *N. England J. Med.* 319:1676–1680). For example, TIL expanded in vitro in the presence of interleukin (IL)-2 have been adoptively transferred to cancer patients, resulting in tumor regression in select patients with metastatic melanoma. Melanoma TIL grown in IL-2 have been identified as activated T lymphocytes $CD3^+$ $HLA-DR^+$, which are predominantly $CD8^+$ cells with unique in vitro antitumor properties. Many long-term melanoma TIL cultures lyse autologous tumors in a specific MHC class I- and T cell antigen receptor dependent manner (Topalian, S. L., et al., 1989, *J. Immunol.* 142:3714). However, studies of TIL derived from other types of tumors have revealed only scant evidence for cytolytic or proliferative antitumor immune specificity (Topalian, S. L. et al., 1990, in *Important Advances in Oncology*, V. T. DeVita, S. A. Hellman and S. A. Rosenberg, eds. J. B. Lippincott, Philadelphia, pp. 19–41). In addition, the toxicity of the high-dose IL-2 + activated lymphocyte treatment advocated by the NCI group has been considerable, including high fevers, severe rigors, hypotension, damage to the endothelial wall due to capillary leak syndrome, and various adverse cardiac events such as arrhythmias and myocardial infarction (Rosenberg S. A., et al., 1988, *N. England J. Med.* 319:1676–1680).

2.1. Tumor-specific Immunogenicities of Heat Shock/Stress Proteins hsp70, hsp90 and gp96

Srivastava et al. demonstrated immune response to methylcholanthrene-induced sarcomas of inbred mice (1988, *Immunol. Today* 9:78–83). In these studies, it was found that the molecules responsible for the individually distinct immunogenicity of these tumors were identified as cell-surface glycoproteins of 96 kDa (gp96) and intracellular proteins of 84 to 86 kDa (Srivastava, P. K., et al., 1986, *Proc. Natl. Acad. Sci. USA* 83:3407–3411; Ullrich, S. J., et al., 1986, *Proc. Natl. Acad. Sci. USA* 83:3121–3125). Immunization of mice with gp96 or p84/86 isolated from a particular tumor rendered the mice immune to that particular tumor, but not to antigenically distinct tumors. Isolation and characterization of genes encoding gp96 and p84/86 revealed significant homology between them, and showed that gp96 and p84/86 were, respectively, the endoplasmic reticular and cytosolic counter parts of the same heat shock proteins (Srivastava, P. K., et al., 1988, *Immunogenetics* 28:205–207; Srivastava, P. K., et al., 1991, *Curr. Top. Microbiol. Immunol.* 167:109–123). Further, hsp70 was shown to elicit immunity to the tumor from which it was isolated but not to antigenically distinct tumors. However, hsp70 depleted of peptides was found to lose its immunogenic activity (Udono, M., and Srivastava, P. K., 1993, *J. Exp. Med.* 178:1391–1396). These observations suggested that the heat shock proteins are not immunogenic per se, but are carriers of antigenic peptides that elicit specific immunity to cancers (Srivastava, P. K., 1993, *Adv. Cancer Res.* 62:153–177).

2.2. Cells Involved in Immune Responses

Cells of the immune system arise from pluripotent stem cells through two main lines of differentiation: a) the lymphoid lineage producing lymphocytes (T cells, B cells natural killer cells), and b) the myeloid lineage producing phagocytes (monocytes, macrophages and neutrophils) and other accessory cells (antigen-presenting cells, platelets, mast cells and endothelial cells) (Roitt I, Brostoff J. and Male D., (eds.), 1993, *Immunology*, Ch. 11, Mosby London).

In the myeloid lineage, the pluripotent stem cells generate colony-forming units (CFU) which can give rise to granulocytes, erythrocytes, monocytes and megakaryocytes (CFU-GEMM). Interleukin-3 and granulocyte-macrophage-colony stimulating factor (GM-CSF) are required for further maturation of granulocytes and monocytes. Thus monocytes present in peripheral blood leukocytes can be activated with GM-CSF in vitro and are capable of becoming macrophages (Gradstein, K. H., et al., 1986, *Science* 232:506–508). Other cytokines, e.g., IL-1, IL-4 and IL-6 promote the differentiation of monocytes into macrophages (Clark S. C. and Kamen R., 1987, *Science* 236:1229–1237).

Thus, macrophages originate in the bone marrow from myeloid stem cells. They circulate in the blood as monocytes and undergo final differentiation to mature tissue macrophages in liver, spleen and lung, among other tissues. Macrophages appear to be major effector cells and leukocytes such as T-lymphocytes and NK cells also play a part in cell-mediated cytotoxicity.

3. SUMMARY OF THE INVENTION

The present invention provides compositions comprising macrophages and/or other antigen presenting cells (APC) sensitized with complexes of heat shock proteins (hsps) non-covalently bound to antigenic molecules, and methods comprising administering such compositions in pharmaceutically acceptable carriers to human subjects with cancer or infectious diseases. The preferred hsps comprised in the complexes suitable for sensitizing the macrophages include, but are not limited to hsp70, hsp90 and gp160 or a combination thereof. Such cells sensitized by complexes comprising hsps and antigenic molecules are herein referred to as "hsp-sensitized" cells.

The present invention encompasses methods for adoptive immunotherapy of cancer and infectious diseases by enhancing the host's immunocompetence and activity of immune effector cells. Adoptive immunotherapy with hsp-sensitized macrophages and other antigen-presenting cells (APC), for example, dendritic cells and B cells (B lymphocytes), induces specific immunity to tumor cells and/or antigenic components, promoting regression of the tumor mass or treatment of immunological disorders or infectious diseases, as the case may be.

The present invention also encompasses methods for the prevention of cancer, infectious diseases and immunological disorders using the adoptive immunotherapy methods of the invention.

In another embodiment, the methods optionally further comprise administering biological response modifiers, e.g., cytokines such as interferon (IFN)-α, IFN-γ, interleukin (IL)-2, IL-4, IL-6, tumor necrosis factor (TNF) or other cytokines and growth factors.

4. BRIEF DESCRIPTION OF FIGURES

Figure 1A:
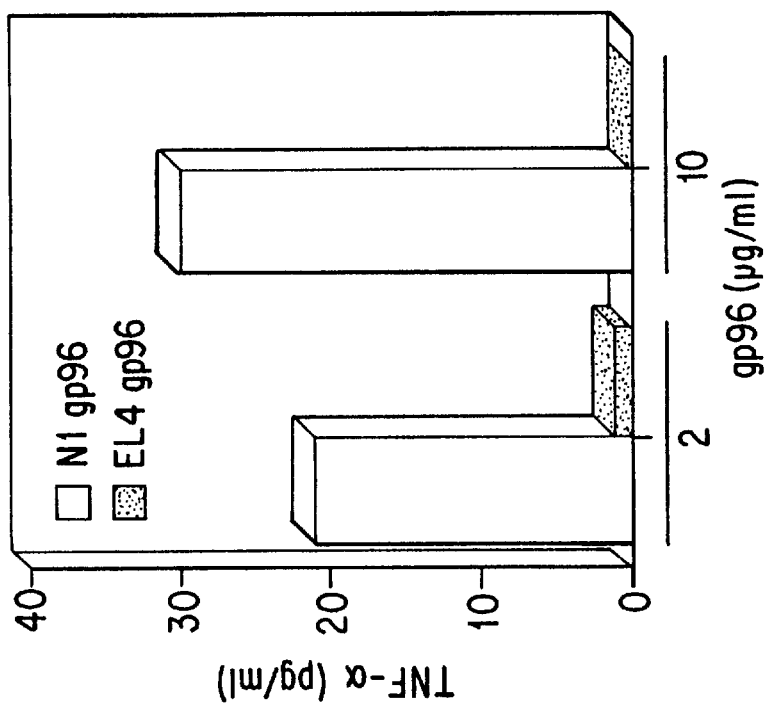
Figure 1C:
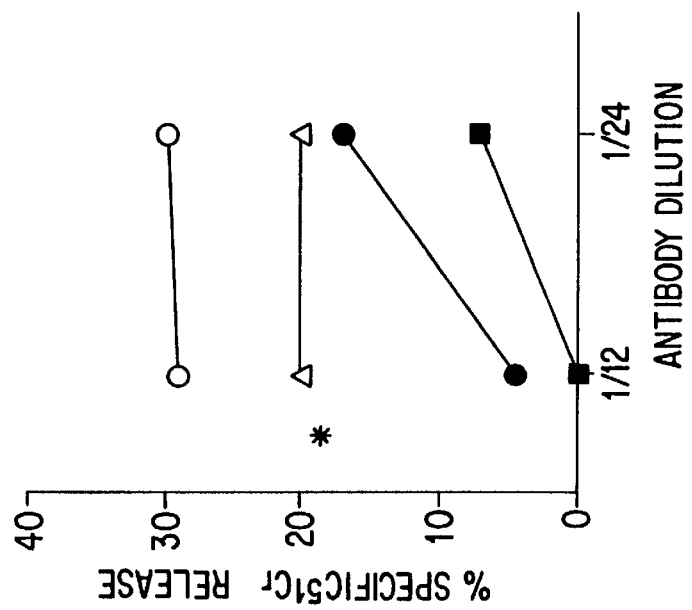

FIGS. 1A–C PEC sensitized with gp96 preparations derived from N1 cells are recognized by VSV-specific cytotoxic T-lymphocytes (CTLs), in $K^b$ - restricted, CD8-mediated manner, but PEC pulsed with gp96 derived from EL4 cells are not. FIG. 1A Pristane-induced PEC ($1 \times 10^4$) from C57BL/6 mice and VSV peptide specific CTL ($5 \times 10^4$) from C57BL/6 mice and VSV peptide specific CTL ($5 \times 10^4$) were co-cultured in presence of gp96 (2 or 10 μg/ml) derived from N1 or EL4 cells in 96-well U-bottom plate at 37° C. After 24 hr supernatants were collected and TNF-α production was measured by bioassay in a cytotoxicity assay using WEHI164 cells. WEHI164 cells were seeded (2,500/well) in flat-bottom 96 well plates. Serially diluted supernatants of PEC-CTL coculture were added. γ-TNF-α was cultured with WEHI 164 in separate wells as control. After 4 hr culture at 37° C., 50 μl MTT (1 mg/ml) was added, with a 4 hr incubation, followed by 100 μl propanol-0.05M HCl. O.D. (590 nm) was measured immediately. Sample concentrations were calculated by comparison with dilution points which resulted in killing of 50% of WEHI164 cells. FIG. 1B The ability of gp96-sensitized macrophage to act as targets in CTL assays was tested. PEC ($5 \times 10^6$/ml) were pulsed with gp96 (10 μg/ml) derived from N1 cells (closed circle), or EL4 cells (open circle), or with VSV nucleocapsid $K^b$ epitope peptide (10 μM) (closed triangle), as a positive control, or medium control (open triangle) for 2 hr at 37° C., followed by labeling with $^{51}Cr$ for 1.5 h. These cells were used as targets in 4 hr $^{51}Cr$-release assay with VSV-specific CTL. FIG. 1C. Anti-CD4 mAb (GK1.5) ascites (open circle), anti-CD8 mAb (YTS1694) (closed square), anti-H-2$K^b$ mAb (Y3) (closed circle), anti-H-2D$^b$ mAb (B22.249) (open triangle) (obtained from American Type Culture Collection, Washington, D.C.) or RPMI control (*) were added to the CTL assay at the same time as effector cells and $^{51}Cr$-labelled PEC pulsed with N1 gp96 (E/T ratio=10).

Figure 2B:
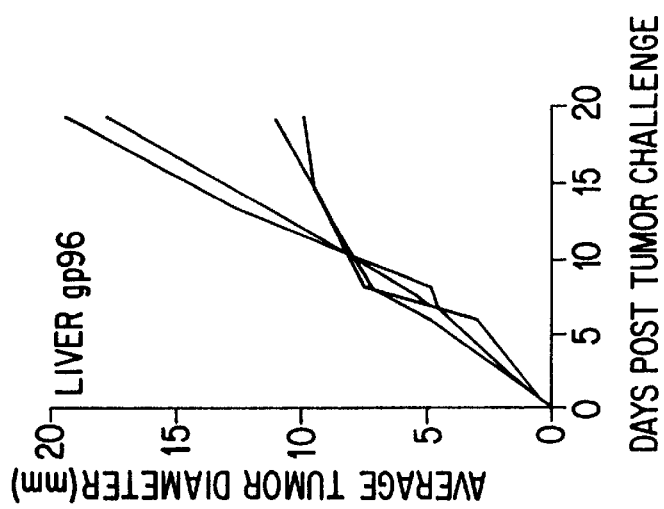
Figure 2A:
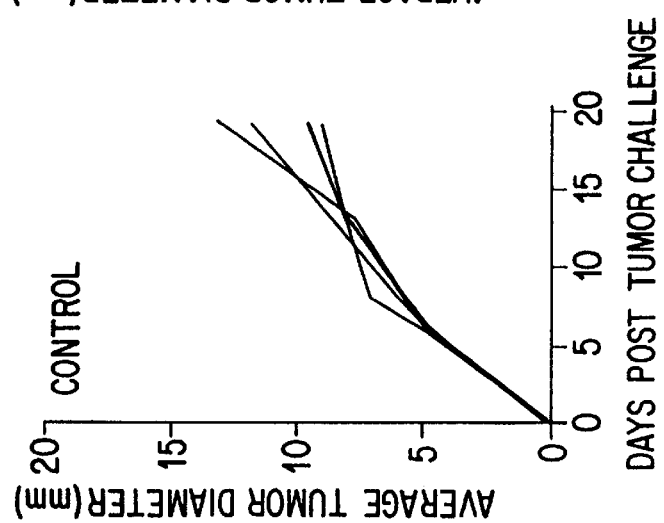
Figure 2E:
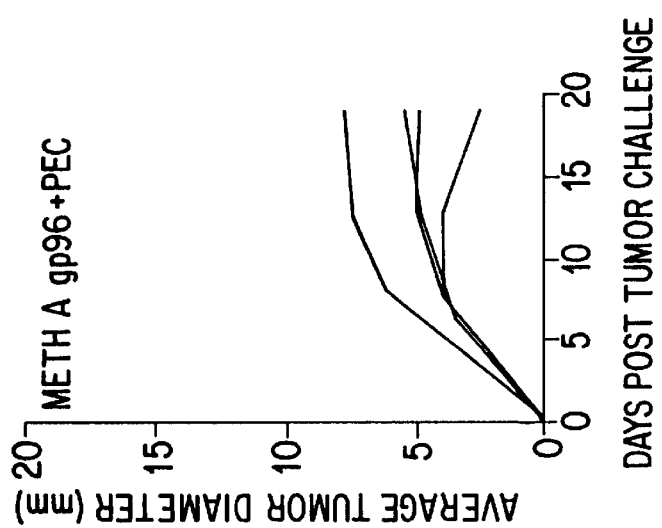
Figure 2D:
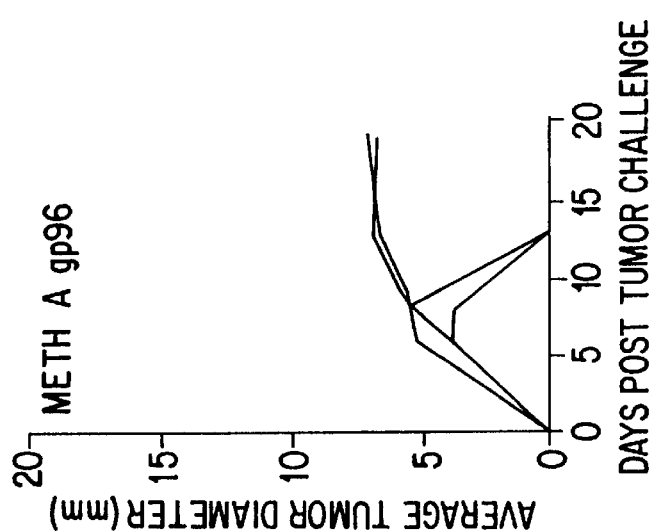
Figure 2C:
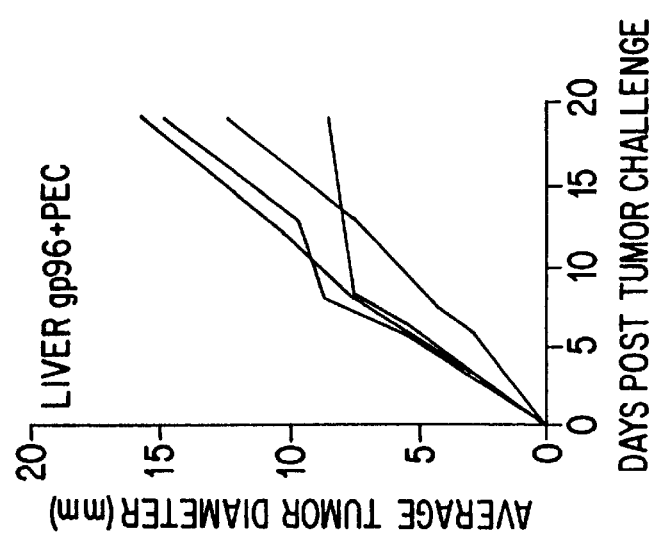

FIGS. 2A–2E. Tumor growth, measured as average tumor diameter in 5 groups of mice challenged with $1 \times 10^5$ cells of Methylcholanthrene (Meth)-A-induced tumor cells treated as follows: FIG. 2A subcutaneous injection of buffer solution; FIG. 2B subcutaneous injection containing 9 μg gp96-peptide complexes derived from liver tissue; FIG. 2C intraperitoneal injection with $5 \times 10^6$ peritoneal exudate cells (PEC) sensitized with 9 μg gp96-peptide complexes derived from normal liver (Liver gp96+PEC); FIG. 2D subcutaneous injection containing 9 μg gp96-peptide complexes derived from Meth A tumor cells; and FIG. 2E intraperitoneal injection with $5 \times 10^6$ PEC sensitized with 9 μg gp96-peptide complexes derived from Meth A tumor cells (Meth A gp96+PEC).

5. DETAILED DESCRIPTION OF THE INVENTION

The present invention pertains to compositions comprising antigen presenting cells (APC) sensitized with complexes of heat shock proteins (hsps) non-covalently bound to antigenic molecules, and therapeutic and prophylactic methods comprising administering such compositions in pharmaceutically acceptable carriers to individuals, preferably human, suffering from cancer, infectious diseases or immunological disorders. The APC can be selected from among those antigen presenting cells known in the art, including but not limited to macrophages, dendritic cells, B lymphocytes, and a combination thereof, and are preferably macrophages. The preferred hsps comprised in the complexes suitable for sensitizing the macrophages and/or APC include, but are not limited to, hsp70, hsp90, gp96 and gp100 or a combination thereof. In a preferred embodiment, the sensitized cells are human cells. In another preferred embodiment, the complexes used to sensitize the cells comprise human hsps and human antigenic molecules. The hsp-sensitized cells can be autologous or non-autologous (eg., allogeneic) to the patient.

In the preferred use of cells autologous to the individual, the use of autologous immune cells such as lymphocytes, macrophages or other APC in adoptive immunotherapy, circumvents a major ethical problem—the issue of whom to select as the donor of the immune cells for adoptive transfer. One cannot immunize normal individuals or even cancer patients in order to obtain immune cells, because of the danger that the inactivated antigenic tumor might grow in the individual who was to be the immunized donor. Another problem circumvented by use of autologous immune cells is graft versus host disease which can be fatal if unsuccessfully treated.

Adoptive immunotherapy according to the invention allows activation of immune cells by incubation with hsp-antigenic molecule complexes, and measurement of reactivity against the tumor or infectious agent in vitro. This in vitro boost followed by clonal selection and/or expansion, and patient infusion constitutes a useful therapeutic/prophylactic strategy.

"Antigenic molecule" as used herein refers to the peptides with which the hsps are endogenously associated in vivo (e.g., in infected cells or precancerous or cancerous tissue) as well as exogenous antigens/immunogens (i.e., with which the hsps are not complexed in vivo) and antigenic/immunogenic fragments and derivatives thereof.

Heat shock proteins, which are also referred to interchangeably herein as stress proteins, useful in the practice of the instant invention can be selected from among any cellular protein that satisfies any one of the following criteria. It is a protein whose intracellular concentration increases when a cell is exposed to a stressful stimuli, it is capable of binding other proteins or peptides, and it is capable of releasing the bound proteins or peptides in the presence of adenosine triphosphate (ATP) or low pH, or it is a protein showing at least 35% homology with any cellular protein having any of the above properties.

The first stress proteins to be identified were the heat shock proteins (hsps). As their name implies, hsps are synthesized by a cell in response to heat shock. To date, three major families of hsp have been identified based on molecular weight. The families have been called hsp60, hsp70 and hsp90 where the numbers reflect the approximate molecular weight of the stress proteins in kilodaltons. Many members of these families were found subsequently to be induced in response to other stressful stimuli including, but not limited to, nutrient deprivation, metabolic disruption, oxygen radicals, and infection with intracellular pathogens. (See Welch, May 1993, *Scientific American* 56–64; Young, 1990, *Annu. Rev. Immunol.* 8:401–420; Craig, 1993, *Science* 260:1902–1903; Gething, et al., 1992, *Nature* 355:33–45; and Lindquist, et al., 1988, *Annu. Rev. Genetics* 22:631–677), the disclosures of which are incorporated herein by reference. It is contemplated that hsps/stress proteins belonging to all of these three families can be used in the practice of the instant invention.

The major hsps can accumulate to very high levels in stressed cells, but they occur at low to moderate levels in cells that have been stressed. For example, the highly inducible mammalian hsp70 is hardly detectable at normal temperatures but becomes one of the most actively synthesized proteins in the cell upon heat shock (Welch, et al., 1985, *J. Cell. Biol.* 101:1198–1211). In contrast, hsp90 and hsp60 proteins are abundant at normal temperatures in most, but not all, mammalian cells and are further induced by heat (Lai, et al., 1984, *Mol. Cell. Biol.* 4:2802–10; van Bergen en Henegouwen, et al., 1987, *Genes Dev.* 1:525–31).

Heat shock proteins are among the most highly conserved proteins in existence. For example, DnaK, the hsp70 from *E. coli* has about 50% amino acid sequence identity with hsp70 proteins from excoriates (Bardwell, et al., 1984, *Proc. Natl. Acad. Sci.* 81:848–852). The hsp60 and hsp90 families also show similarly high levels of intra families conservation (Hickey, et al., 1989, *Mol. Cell. Biol.* 9:2615–2626; Jindal, 1989, *Mol. Cell. Biol.* 9:2279–2283). In addition, it has been discovered that the hsp60, hsp70 and hsp90 families are composed of proteins that are related to the stress proteins in sequence, for example, having greater than 35% amino acid identity, but whose expression levels are not altered by stress. Therefore it is contemplated that the definition of stress protein, as used herein, embraces other proteins, muteins, analogs, and variants thereof having at least 35% to 55%, preferably 55% to 75%, and most preferably 75% to 85% amino acid identity with members of the three families whose expression levels in a cell are enhanced in response to a stressful stimulus. The purification of stress proteins belonging to these three families is described below.

The hsp-antigenic molecule complexes used to sensitize APCs according to the invention may include any complex containing an hsp and a molecule that is capable of inducing an immune response in a mammal. The antigenic/immunogenic molecules are noncovalently associated with the hsp. Preferred complexes include, but are not limited to, hsp60-peptide, hsp70-peptide and hsp90-peptide complexes, in which the hsp-peptide complex is present in vivo and is isolated from cells. In a specific embodiment, the complex comprises an hsp called gp96 which is present in the endoplasmic reticulum of eukaryotic cells and is related to the cytoplasmic hsp90's.

Although the hsps can be allogeneic to the patient, in a referred embodiment, the hsps are autologous to (derived from) the patient to whom they are administered. The hsps and/or antigenic molecules can be purified from natural sources, chemically synthesized, or recombinantly produced.

The present invention encompasses methods for adoptive immunotherapy of cancer, infectious diseases and immunological disorders by enhancing the host's immunocompetence activity of immune effector cells. Adoptive immunotherapy with macrophages and other APC for example, dendritic cells and B-cells, sensitized hsps and antigenic molecules, induces specific immunity to tumor cells and/or infectious agents (depending upon the identity of antigenic molecule) and leads to regression of the tumor mass and/or infectious disease, respectively.

Cancers which are responsive to adoptive immunotherapy by the hsp complex-sensitized macrophages and/or APC of the invention include, but are not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease.

The invention also provides a kit comprising in a container a complex of an hsp noncovalently bound to an exogenous antigenic molecule. The kit can further comprise in a second container human APC.

5.1 Complexes for Sensitizing APC

In accordance with the methods described herein, APC are sensitized with hsp complexed with immunogenic or antigenic molecules that are endogenously complexed to hsps or MHC antigens and can be used as antigenic molecules. For example, such peptides may be prepared that stimulate cytotoxic T cell responses against different tumor specific antigens (e.g., tyrosinase, gp100, melan-A, gp75, mucins, etc.) and viral proteins including, but not limited to, proteins of immunodeficiency virus type I (HIV-I), human immunodeficiency virus type II (HIV-II), hepatitis type A, hepatitis type B, hepatitis type C, influenza, Varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus and polio virus. In the embodiment wherein the antigenic molecules are peptides noncovalently complexed to hsps in vivo, the complexes can be isolated from cells, or alternatively, produced in vitro from purified preparations each of hsps and antigenic molecules.

In another specific embodiment, antigens of cancers (e.g., tumors) or infectious agents (e.g., viral antigen, bacterial antigens, etc.) can be obtained by purification from natural sources, by chemical synthesis, or recombinantly, and, through in vitro procedures such as that described below, noncovalently complexed to hsps.

In an embodiment wherein the hsp-antigenic molecule complex to be used is a complex that is produced in vivo in cells, exemplary purification procedures such as described in Sections 5.1.1–5.1.3 below can be employed. Alternatively, in an embodiment wherein one wishes to use antigenic molecules by complexing to hsps in vitro, hsps can be purified for such use from the endogenous hsp-peptide complexes in the presence of ATP or low pH (or chemically synthesized or recombinantly produced). The protocols described herein may be used to isolate hsp-peptide complexes, or the hsps alone, from any eukaryotic cells for example, tissues, isolated cells, or immortalized eukaryote cell lines infected with a preselected intracellular pathogen, tumor cells or tumor cell lines.

5.1.1. Preparation and Purification of Hsp 70-peptide Complexes

The purification of hsp 70-peptide complexes has been described previously, see, for example, Udono et al., 1993, J. Exp. Med. 178:1391–1396. A procedure that may be used, presented by way of example but not limitation, is as follows:

Initially, tumor cells are suspended in 3 volumes of 1× Lysis buffer consisting of 5 mM sodium phosphate buffer (pH7), 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000 g for 90 minutes, the supernatant harvested and then mixed with Con A SEPHAROSE™ equilibrated with phosphate buffered saline (PBS) containing 2 mM $Ca^{2+}$ and 2 mM $Mg^{2+}$. When the cells are lysed by mechanical shearing the supernatant is diluted with an equal volume of 2× Lysis buffer prior to mixing with Con A SEPHAROSE™. The supernatant is then allowed to bind to the Con A SEPHAROSE™ for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a MONO Q FPLIC™ ion exchange chromatographic column (Pharmacia) equilibrated in 20 mM Tris Acetate pH 7.5, 20 mM NaCl, 0.1 mM EDTA and 15 mM 2-mercaptoethanol. The column is then developed with a 20 mM to 500 mM NaCl gradient and then eluted fractions fractionated by sodium dodecyl sulfate-polyacrylamide gel electrophoresis (SDS-PAGE) and characterized by immunoblotting using an appropriate anti-hsp70 antibody (such as from clone N27F3-4, from StressGen).

Fractions strongly immunoreactive with the anti-hsp70 antibody are pooled and the hsp70-peptide complexes precipitated with ammonium sulfate; specifically with a 50%–70% ammonium sulfate cut. The resulting precipitate is then harvested by centrifugation at 17,000 rpm (SS34 Sorvall rotor) and washed with 70% ammonium sulfate. The washed precipitate is then solubilized and any residual ammonium sulfate removed by gel filtration on a Sephadex$^R$ G25 column (Pharmacia). If necessary the hsp70 preparation thus obtained can be repurified through the MONO Q FPLIC™ ion exchange chromatographic column (Pharmacia) as described above.

The hsp70-peptide complex can be purified to apparent homogeneity using this method. Typically 1 mg of hsp70-peptide complex can be purified from 1 g of cells/tissue.

The present invention further describes a new and rapid method for purification of hsp70-peptide complexes. This improved method uses chromatography with ADP affixed to a solid substratum (e.g., ADP-agarose). The resulting hsp70 preparations are higher in purity and devoid of peptides. The hsp70 yields are also increased significantly by about more than 10 fold. Alternatively, chromatography with nonhydrolyzable analogs of ATP, instead of ADP, can be used in chromatography for purification of hsp70-peptide complexes. By way of example but not limitation, purification of hsp70-peptide complexes by ADP-agarose chromatography was carried out as follows: Meth A sarcoma cells (500 million cells) were homogenized in hypotonic buffer and the lysate was centrifuged at 100,000 g for 90 minutes at 4° C. The supernatant was divided into two and was applied to an ADP-agarose or an ATP-agarose column. The columns were washed in buffer and were eluted with 3 ADP or 3 mM ATP, respectively. The eluted fractions were analyzed by SDS-PAGE: in both cases, apparently homogeneous preparations of hsp70 were obtained. However, when each of the preparations was tested for presence of peptides, the ADP-bound/eluted hsp70 preparation was found to be associated with peptides, while the ATP-bound/eluted hsp70 preparation was not.

5.1.2. Preparation and Purification of Hsp 90-peptide Complexes

A procedure that can be used, presented by way of example and not limitation, is as follows:

Initially, tumor cells are suspended in 3 volumes of 1× Lysis buffer consisting of 5 mM sodium phosphate buffer pH 7, 150 mM NaCl, 2 mM $CaCl_2$, 2 mM $MgCl_2$ and 1 mM phenyl methyl sulfonyl fluoride (PMSF). Then, the pellet is sonicated, on ice, until >99% cells are lysed as determined by microscopic examination. As an alternative to sonication, the cells may be lysed by mechanical shearing and in this approach the cells typically are resuspended in 30 mM sodium bicarbonate pH 7.5, 1 mM PMSF, incubated on ice for 20 minutes and then homogenized in a dounce homogenizer until >95% cells are lysed.

Then the lysate is centrifuged at 1,000 g for 10 minutes to remove unbroken cells, nuclei and other cellular debris. The resulting supernatant is recentrifuged at 100,000g for 90 minutes, the supernatant harvested and then mixed with Con A SEPHAROSE™ equilibrated with PBS containing 2 mM $Ca^{2+}$ and 2 mM $Mg^{2+}$. When the cells are lysed by mechanical shearing the supernatant is diluted with an equal volume of 2x Lysis buffer prior to mixing with Con A SEPHAROSE™. The supernatant is then allowed to bind to the Con A SEPHAROSE™ for 2–3 hours at 4° C. The material that fails to bind is harvested and dialyzed for 36 hours (three times, 100 volumes each time) against 10 mM Tris-Acetate pH 7.5, 0.1 mM EDTA, 10 mM NaCl, 1 mM PMSF. Then the dialyzate is centrifuged at 17,000 rpm (Sorvall SS34 rotor) for 20 minutes. Then the resulting supernatant is harvested and applied to a MONO Q FPLC™ ion exchange chromatographic column (Pharmacia) equilibrated with lysis buffer. The proteins are then eluted with a salt gradient of 200 mM to 600 mM NaCl.

The eluted fractions are fractionated by SDS-PAGE and fractions containing the hsp90-peptide complexes identified by immunoblotting using an anti-hsp90 antibody such as 3G3 (Affinity Bioreagents). Hsp90-peptide complexes can be purified to apparent homogeneity using this procedure. Typically, 150–200 μg of hsp90-peptide complex can be purified from ig of cells/tissue.

5.1.3. Preparation and Purification of gp96-peptide Complexes

A procedure that can be used, presented by way of example and not limitation, is as follows:

A pellet of tumors is resuspended in 3 volumes of buffer consisting of 30 mM sodium bicarbonate buffer (pH 7.5) and 1 mM PMSF and the cells allowed to swell on ice 20 minutes. The cell pellet then is homogenized in a Dounce homogenizer (the appropriate clearance of the homogenizer will vary according to each cells type) on ice until >95% cells are lysed.

The lysate is centrifuged at 1,000 g for 10 minutes to remove unbroken cells, nuclei and other debris. The supernatant from this centrifugation step then is recentrifuged at 100,000 g for 90 minutes. The gp96-peptide complex can be purified either from the 100,000 g pellet or from the supernatant.

When purified from the supernatant, the supernatant is diluted with equal volume of 2x lysis buffer and the supernatant mixed for 2–3 hours at 4° C. with Con A SEPHAROSE™ equilibrated with PBS containing 2 mM $Ca^{2+}$ and 2 mM $Mg^{2+}$. Then, the slurry is packed into a column and washed with 1x lysis buffer until the $OD_{280}$ drops to baseline. Then, the column is washed with ⅓ column bed volume of 10% α-methyl mannoside (α-MM) dissolved in PBS containing 2 mM $Ca^{2+}$ and 2 mM $Mg^{2+}$, the column sealed with a piece of parafilm, and incubated at 37° C. for 15 minutes. Then the column is cooled to room temperature and the parafilm removed from the bottom of the column. Five column volumes of the α-MM buffer are applied to the column and the eluate analyzed by SDS-PAGE. Typically the resulting material is about 60–95% pure; however, this depends upon the cell type and the tissue-to-lysis buffer ratio used. Then the sample is applied to a MONO Q FPLC™ ion exchange chromatographic (Pharmacia) equilibrated with a buffer containing 5 mM sodium phosphate, pH 7. The proteins then are eluted from the column with a 0–1M NaCl gradient and the gp96 fraction elutes between 400 mM and 550 mM NaCl.

The procedure, however, may be modified by two additional steps, used either alone or in combination, to consistently produce apparently homogeneous gp96-peptide complexes. One optional step involves an ammonium sulfate precipitation prior to the Con A purification step and the other optional step involves DEAE-SEPHAROSE™ purification after the Con A purification step but before the MONO Q FPLC™ ion exchange chromatography step.

In the first optional step, the supernatant resulting from the 100,000 g centrifugation step is brought to a final concentration of 50% ammonium sulfate by the addition of ammonium sulfate. The ammonium sulfate is added slowly while gently stirring the solution in a beaker placed in a tray of ice water. The solution is stirred from about ½ to 12 hours at 4° C. and the resulting solution centrifuged at 6,000 rpm (Sorvall SS34 rotor). The supernatant resulting from this step is removed, brought to 70% ammonium sulfate saturation by the addition of ammonium sulfate solution, and centrifuged at 6,000 rpm (Sorvall SS34 rotor). The resulting pellet from this step is harvested and suspended in PBS containing 70% ammonium sulfate in order to rinse the pellet. This mixture is centrifuged at 6,000 rpm (Sorvall SS34 rotor) and the pellet dissolved in PBS containing 2 mM $Ca^{2+}$ and $Mg^{2+}$. Undissolved material is removed by a brief centrifugation at 15,000 rpm (Sorvall SS34 rotor). Then, the solution is mixed with Con A SEPHAROSE™ and the procedure followed as before.

In the second optional step, the gp96 containing fractions eluted from the Con A column are pooled and the buffer exchanged for 5 mM sodium phosphate buffer, pH 7, 300 mM NaCl by dialysis, or preferably by buffer exchange on a SEPHADEX™ G25 column. After buffer exchange, the solution is mixed with DEAE-SEPHAROSE™ previously equilibrated with 5 mM sodium phosphate buffer, pH 7, 300 mM NaCl. The protein solution and the beads are mixed gently for 1 hour and poured into a column. Then, the column is washed with 5 mM sodium phosphate buffer, pH 7, 300 mM NaCl, until the absorbance at 280 mM drops to baseline. Then, the bound protein is eluted from the column with five volumes of 5 mM sodium phosphate buffer, pH 7, 700 mM NaCl. Protein containing fractions are pooled and diluted with 5 mM sodium phosphate buffer, pH 7 in order to lower the salt concentration to 175 mM. The resulting material then is applied to the MONO Q FPLC™ ion exchange chromatographic column (Pharmacia) equilibrated with 5 mM sodium phosphate buffer, pH 7 and the protein that binds to the MONO Q FPLC™ ion exchange chromatographic column (Pharmacia) is eluted as described before.

It is appreciated, however, that one skilled in the art may assess, by routine experimentation, the benefit of incorporating the second optional step into the purification protocol. In addition, it is appreciated also that the benefit of adding each of the optional steps will depend upon the source of the starting material.

When the gp96 fraction is isolated from the 100,000 g pellet, the pellet is suspended in 5 volumes of PBS containing either 1% sodium deoxycholate or 1% oxtyl glucopyranoside (but without the $Mg^{2+}$ and $Ca^{2+}$) and incubated on ice for 1 hour. The suspension is centrifuged at 20,000 g for 30 minutes and the resulting supernatant dialyzed against several changes of PBS (also without the $Mg^{2+}$ and $Ca^{2+}$) to remove the detergent. The dialysate is centrifuged at 100,000 g for 90 minutes, the supernatant harvested, and calcium and magnesium are added to the supernatant to give final concentrations of 2 mM, respectively. Then the sample is purified by either the unmodified or the modified method for isolating gp96-peptide complex from the 100,000 g supernatant, see above.

The gp96-peptide complexes can be purified to apparent homogeneity using this procedure. About 10–20 μg of gp96 can be isolated from 1 g cells/tissue.

Infectious Disease

In an alternative embodiment wherein it is desired to treat a patient having an infectious disease or prevent an infectious disease, the above-described methods in Sections 5.1.1–5.1.3 are used to isolate hsp-peptide complexes from cells infected with an infectious organism, e.g., of a cell line or from a patient. Such infectious organisms include but are not limited to, viruses, bacterial, protozoa, fungi, and parasites as described in detail below.

5.1.4. Isolation of Antigenic Molecules From Endogenous Complexes of Hsps or MHC Antigens It has been found that antigenic peptides and/or components can be eluted from endogenous, in vivo hsp-complexes either in the presence of ATP or low pH. These experimental conditions may be used to isolate peptides and/or antigenic components from cells which may contain potentially useful antigenic determinants. Once isolated, the amino acid sequence of each antigenic peptide may be determined using conventional amino acid sequencing methodologies. Such antigenic molecules can then be produced by chemical synthesis or recombinant methods, purified, and complexed to hsps in vitro.

Similarly, it has been found that potentially immunogenic peptides may be eluted from MHC-peptide complexes using techniques well known in the art (Falk, K. et al., 1990 *Nature* 348:248–251; Elliott, T., et al., 1990, *Nature* 348:195–197; Falk, K., et al., 1991, *Nature* 351:290–296).

Thus, potentially immunogenic or antigenic peptides may be isolated from either endogenous stress protein-peptide complexes or endogenous MHC-peptide complexes for use subsequently as antigenic molecules, by complexing in vitro to hsps. Exemplary protocols for isolating peptides and/or antigenic components from either of the these complexes are set forth below.

5.1.4.1 Peptides From Stress Protein-Peptide Complexes

Two methods may be used to elute the peptide from a stress protein-peptide complex. One approach involves incubating the stress protein-peptide complex in the presence of ATP. The other approach involves incubating the complexes in a low pH buffer.

Briefly the complex of interest is centrifuged through a CENTRICON™ 10 assembly (Millipore) to remove any low molecular weight material loosely associated with the complex. The large molecular weight fraction may be removed and analyzed by SDS-PAGE while the low molecular weight may be analyzed by HPLC as described below. In the ATP incubation protocol, the stress protein-peptide complex in the large molecular weight fraction is incubated with 10 mM ATP for 30 minutes at room temperature. In the low pH protocol, acetic acid or trifluoroacetic acid is added to the stress protein-peptide complex to give a final concentration of 10% (vol/vol) and the mixture incubated at room temperature in a boiling water bath or any temperature in between for 10 minutes (See, Van Bleek, et al., 1990, *Nature* 348:213–216; and Li, et al., 1993, *EMBO Journal* 12:3143–3151).

The resulting samples are centrifuged through an CENTRICON™ 10 assembly as mentioned previously. The high and low molecular weight fractions are recovered. The remaining large molecular weight stress protein-peptide complexes can be reincubated with ATP or low pH to remove any remaining peptides.

The resulting lower molecular weight fractions are pooled, concentrated by evaporation and dissolved in 0.1% trifluoroacetic acid (TFA). The dissolved material is then fractionated by reverse phase high pressure liquid chromatography (HPLC) using for example a VYDAC CIB reverse phase column equilibrated with 0.1% TFA. The bound material is then eluted at a flow rate of about 0.8 ml/min by developing the column with a linear gradient of 0 to 80% acetonitrile in 0.1% TFA. The elution of the peptides can be monitored by $OD_{210}$ and the fractions containing the peptides collected.

5.1.4.2 Peptides from MHC-peptide Complexes

The isolation of potentially immunogenic peptides from MHC molecules is well known in the art and so is not described in detail herein (See, Falk, et al., 1990, *Nature* 348:248–251; Rotzsche, at al., 1990, *Nature* 348:252–254; Elliott, et al., 1990, *Nature* 348:191–197; Falk, et al., 1991, *Nature* 351:290–296; Demotz, et al., 1989, *Nature* 343:682–684; Rotzsche, et al., 1990, *Science* 249:283–287), the disclosures of which are incorporated herein by reference.

Briefly, MHC-peptide complexes may be isolated by a conventional immunoaffinity procedure. The peptides then may be eluted from the MHC-peptide complex by incubating the complexes in the presence of about 0.1% TFA in acetonitrile. The eluted peptides may be fractionated and purified by reverse phase HPLC, as before.

The amino acid sequences of the eluted peptides may be determined either by manual or automated amino acid sequencing techniques well known in the art. Once the amino acid sequence of a potentially protective peptide has been determined the peptide may be synthesized in any desired amount using conventional peptide synthesis or other protocols well known in the art.

Peptides having the same amino acid sequence as those isolated above may be synthesized by solid-phase peptide synthesis using procedures similar to those described by Merrifield, 1963, *J. Am. Chem. Soc.*, 85:2149. During synthesis, N-α-protected amino acids having protected side chains are added stepwise to a growing polypeptide chain linked by its C-terminal and to an insoluble polymeric support i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. The N-α-protecting group is then removed. The deprotected α-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, Atherton, et al., 1989, *Solid Phase Peptide Synthesis: A Practical Approach*, IRL Press, and Bodanszky, 1993, *Peptide Chemistry, A Practical Textbook*, 2nd Ed., Springer-Verlag).

Purification of the resulting peptides is accomplished using conventional procedures, such as preparative HPLC using gel permeation, partition and/or ion exchange chromatography. The choice of appropriate matrices and buffers are well known in the art and so are not described in detail herein.

5.1.5 Exogenous Antigenic Molecules

Antigens or antigenic portions thereof can be selected for use as antigenic molecules, for complexing to hsps, from among those known in the art or determined by immunoassay to be able to bind to antibody or MHC molecules (antigenicity) or generate immune responses (immunogenicity). To determine immunogenicity or antigenicity by detecting binding to antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitin reactions, immunodiffusion assays, in vivo immunoassays (using colloidal gold, enzyme or radioisotope labels, for example), western blots, immunoprecipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labelled. Many means are known in the art for detecting binding in an immunoassay and are envisioned for use. In one embodiment for detecting immunogenicity, T cell-mediated responses can be assayed by standard methods, e.g., in vitro cytotoxicity assays or in vivo delayed-type hypersensitivity assays.

Potentially useful antigens or derivatives thereof for use as antigenic molecules can also be identified by various criteria, such as the antigen's involvement in neutralization of a pathogen's infectivity (wherein it is desired to treat or prevent infection by such a pathogen) (Norrby, 1985, *Summary*, in Vaccines 85, Lerner, et al. (eds.), Cold Spring Harbor Laboratory, Cold Spring Harbor, N.Y., pp. 388–389), type or group specificity, recognition by patients' antisera or immune cells, and/or the demonstration of protective effects of antisera or immune cells specific for the antigen. In addition, where it is desired to treat or prevent a disease caused by pathogen, the antigen's encoded epitope should preferably display a small or no degree of antigenic variation in time or amongst different isolates of the same pathogen.

Preferably, where it is desired to treat or prevent cancer, known tumor-specific antigens or fragments or derivatives thereof are used. For example, such tumor specific or tumor-associated antigens include, but are not limited to, KS ¼ pan-carcinoma antigen (Perez and Walker, 1990, *J. Immunol.* 142:3662–3667; Bumal, 1988, *Hybridoma* 7(4):407–415); ovarian carcinoma antigen (CA125) (Yu, et al., 1991, *Cancer Res.* 51(2):468–475); prostatic acid phosphate (Tailer, et al., 1990, *Nucl. Acids Res.* 18(16):4928); prostate specific antigen (Henttu and Vihko, 1989, *Biochem. Biophys. Res. Comm.* 160(2):903–910; Israeli, et al., 1993, *Cancer Res.* 53:227–230); melanoma-associated antigen p97 (Estin, et al., 1989, *J. Natl. Cancer Inst.* 81(6):445–446); melanoma antigen gp75 (Vijayasardahl, et al., 1990, *J. Exp. Med.* 171(4):1375–1380); high molecular weight melanoma antigen (Natali, et al., 1987, *Cancer* 59:55–63) and prostate specific membrane antigen.

In a specific embodiment, an antigen or fragment or derivative thereof specific to a certain tumor is selected for complexing to hsp and subsequent sensitization of APC.

Preferably, where it is desired to treat or prevent viral diseases, molecules comprising epitopes of known viruses are used as antigenic molecules. For example, such antigenic epitopes may be prepared from viruses including, but not limited to, hepatitis type A hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, Coxsachie virus, mumps virus, measles virus, rubella virus, polio virus, human immunodeficiency virus type I (HIV-I), and human immunodeficiency virus type II (HIV-II). Preferably, where it is desired to treat or prevent bacterial infections, molecules comprising epitopes of known bacteria are used. For example, such antigenic epitopes may be prepared from bacteria including, but not limited to, mycobacteria rickettsia, mycoplasma, neisseria and legionella.

Preferably, where it is desired to treat or prevent protozoal infectious, molecules comprising epitopes of known protozoa are used as antigenic molecules. For example, such antigenic epitopes may be prepared from protozoa including, but not limited to, leishmania, kokzidioa, and trypanosoma.

Preferably, where it is desired to treat or prevent parasitic infections, molecules comprising epitopes of known parasites are used as antigenic molecules. For example, such antigenic epitopes may be from parasites including, but not limited to, chlamydia and rickettsia.

5.2 In Vitro Production of Stress Protein-Antigenic Molecule Complexes

In an embodiment in which complexes of hsps and the peptides with which they are endogenously associated in vivo are not employed, complexes of hsps to antigenic molecules are produced in vitro. As will be appreciated by those skilled in the art, the peptides either isolated by the aforementioned procedures or chemically synthesized or recombinantly produced may be reconstituted with a variety of naturally purified or recombinant stress proteins in vitro to generate immunogenic non-covalent stress protein-antigenic molecule complexes. Alternatively, exogenous antigens or antigenic/immunogenic fragments or derivatives thereof can be noncovalently complexed to stress proteins for use in the immunotherapeutic or prophylactic vaccines of the invention. A preferred, exemplary protocol for noncovalently complexing a stress protein and an antigenic molecule in vitro is discussed below.

Prior to complexing, the hsps are pretreated with ATP or low pH to remove any peptides that may be associated with the hsp of interest. When the ATP procedure is used, excess ATP is removed from the preparation by the addition of apyranase as described by Levy, et al., 1991, *Cell* 67:265–274. When the low pH procedure is used, the buffer is readjusted to neutral pH by the addition of pH modifying reagents.

The antigenic molecules (1 $\mu$g) and the pretreated hsp (9 $\mu$g) are admixed to give an approximately 5 antigenic molecule: 1 stress protein molar ratio. Then, the mixture is incubated for 15 minutes to 3 hours at 40°–45° C. in a suitable binding buffer, for example, one containing 20 mM sodium phosphate, pH 7.2, 350 mM NaCl, 3 mM $MgCl_2$ and 1 mM phenyl methyl sulfonyl fluoride (PMSF). The preparations are centrifuged through Centricon 10 assembly (Millipore) to remove any unbound peptide. The association of the peptides with the stress proteins can be assayed by SDS-PAGE. This is the preferred method for in vitro complexing of peptides isolated from MHC-peptide complexes of peptides disassociated from endogenous hsp-peptide complexes.

In an alternative embodiment of the invention, preferred for producing complexes of hsp70 to exogenous antigenic molecules such as proteins, 5–10 micrograms of purified hsp is incubated with equimolar quantities of the antigenic molecule in 20 mM sodium phosphate buffer pH 7.5, 0.5M NaCl, 3 mM $MgCl_2$ and 1 mM ADP in a volume of 100 microliter at 37° C. for 1 hr. This incubation mixture is further diluted to 1 ml in phosphate-buffered saline.

In an alternative embodiment of the invention, preferred for producing complexes of gp96 or hsp90 to peptides, 5–10 micrograms of purified gp96 or hsp90 is incubated with equimolar or excess quantities of the antigenic peptide in a suitable buffer such as one containing 20 mM sodium phosphate buffer, pH 7.5, 0.5M NaCl, 3 mM $MgCl_2$ at 60°–65° C. for 5–20 minutes. This incubation mixture is allowed to cool to room temperature and centrifuged more than once, if necessary through Centricon 10 assembly (Millipore) to remove any unbound peptide.

Following complexing, the stress protein-antigenic molecule complexes can optionally be assayed in vitro for immunogenicity, using for example the mixed lymphocyte target cell assay (MLTC) described below.

5.2.1 Determination of Immunogenicity of Stress Protein-Peptide Complexes

The purified stress protein-antigenic molecule complexes can optionally be assayed for immunogenicity using the mixed lymphocyte target culture assay (MLTC) well known in the art, prior to their use to sensitize APC. It will be understood that this procedure is entirely optional, and not necessary to practice the present invention.

By way of example but not limitation, the following procedure can be used. Briefly, mice are injected subcutaneously with the candidate stress protein-antigenic molecule complexes. Other mice are injected with either other stress protein peptide complexes or whole infected cells which act as positive controls for the assay. The mice are injected twice, 7–10 days apart. Ten days after the last immunization, the spleens are removed and the lymphocytes released. The released lymphocytes may be restimulated subsequently in vitro by the addition of dead cells that expressed the complex of interest.

For example, $8\times10^6$ immune spleen cells may be stimulated with $4\times10^4$ mitomycin C treated or γ-irradiated (5–10,000 rads) infected cells (or cells transfected with an appropriate gene, as the case may be) in 3 ml RPMI medium containing 10% fetal calf serum. In certain cases 33% secondary mixed lymphocyte culture supernatant may be included in the culture medium as a source of T cell growth factors (See, Glasebrook, et al., 1980, J. Exp. Med. 151:876). To test the primary cytotoxic T cell response after immunization, spleen cells may be cultured without stimulation. In some experiments spleen cells of the immunized mice may also be restimulated with antigenically distinct cells, to determine the specificity of the cytotoxic T cell response.

Six days later the cultures are tested for cytotoxicity in a 4 hour $^{51}$Cr-release assay (See, Palladino, et al., 1987, Cancer Res. 47:5074–5079 and Blachere, at al., 1993, J. Immunotherapy 14:352–356). In this assay, the mixed lymphocyte culture is added to a target cell suspension to give different effector:target (E:T) ratios (usually 1:1 to 40:1).

The target cells are prelabelled by incubating $1\times10^6$ target cells in culture medium containing 200 mCi $^{51}$Cr/ml for one hour at 37° C. The cells are washed three times following labeling. Each assay point (E:T ratio) is performed in triplicate and the appropriate controls incorporated to measure spontaneous $^{51}$Cr release (no lymphocytes added to assay) and 100% release (cells lysed with detergent). After incubating the cell mixtures for 4 hours, the cells are pelleted by centrifugation at 200 g for 5 minutes. The amount of $^{51}$Cr released into the supernatant is measured by a gamma counter. The percent cytotoxicity is measured as cpm in the test sample minus spontaneously released cpm divided by the total detergent released cpm minus spontaneously released cpm.

In order to block the MHC class I cascade a concentrated hybridoma supernatant derived from K-44 hybridoma cells (an anti-MHC class I hybridoma) is added to the test samples to a final concentration of 12.5%.

5.3. Obtaining Macrophages and Antigen-Presenting Cells

The antigen-presenting cells, including but not limited to macrophages, dendritic cells and B-cells, are preferably obtained by production in vitro from stem and progenitor cells from human peripheral blood or bone marrow as described by Inaba, K., et al., 1992, J. Exp. Med. 176:1693–1702.

APC can be obtained by any of various methods known in the art. In a preferred aspect human macrophages are used, obtained from human blood cells. By way of example but not limitation, macrophages can be obtained as follows:

Mononuclear cells are isolated from peripheral blood of a patient (preferably the patient to be treated), by Ficoll-Hypaque gradient centrifugation.

Tissue culture dishes are pre-coated with the patient's own serum or with other AB+ human serum and incubated at 37° C. for 1 hr. Non-adherent cells are removed by pipetting. To the adherent cells left in the dish, is added cold (4° C.) 1 mM EDTA in phosphate-buffered saline and the dishes are left at room temperature for 15 minutes. The cells are harvested, washed with RPMI buffer and suspended in RPMI buffer. Increased numbers of macrophages may be obtained by incubating at 37° C. with macrophage-colony stimulating factor (M-CSF); increased numbers of dendritic cells may be obtained by incubating with granulocyte-macrophage-colony stimulating factor (GM-CSF) as described in detail by Inaba, K., et al., 1992, J. Exp. Med. 176:1693–1702.

5.4. Sensitization of Macrophages and Antigen Presenting Cells with Hsp-Complexes APC are sensitized with hsp non-covalently bound to antigenic molecules by incubating the cells in vitro with the complexes. The APC are sensitized with complexes of hsps and antigenic molecules by incubating in vitro with the hsp-complex at 37° C. for 15 min.–24 hrs. By way of example but not limitation, $4\times10^7$ macrophages can be incubated with 10 microgram gp96-peptide complexes per ml or 100 microgram hsp90-peptide complexes per ml at 37° C. for 15 min.–24 hrs. in 1 ml plain RPMI medium. The cells are washed three times and resuspended in a physiological medium preferably sterile, at a convenient concentration (e.g., $1\times10^7$/ml) for infusion in a patient. Preferably, the patient into which the sensitized APCs are infused is the patient from which the APC were originally isolated (autologous embodiment).

Optionally, the ability of sensitized APC to stimulate, for example, the antigen-specific, class I-restricted cytotoxic T-lymphocytes (CTL) can be monitored by their ability to stimulate CTLs to release tumor necrosis factor, and by their ability to act as targets of such CTLs, as described below in Example 6, below.

5.5. Reinfusion of Sensitized APC

The hsp-sensitized macrophages and other APC are reinfused into the patient systemically, preferably intravenously, by conventional clinical procedures. These activated cells are reinfused, preferentially by systemic administration into the autologous patient. Patients generally receive from about $10^6$ to about $10^{12}$ sensitized macrophages, depending on the condition of the patient. In some regimens, patients may optionally receive in addition a suitable dosage of a biological response modifier including but not limited to the cytokines IFN-α, IFN-α, IL-2, IL-4, IL-6, TNF or other cytokine growth factor.

5.6 Target Infectious Diseases

Infectious diseases that can be treated or prevented by the methods of the present invention are caused by infectious agents including but not limited to viruses, bacteria, fungi, protozoa and parasites.

Viral diseases that can be treated or prevented by the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsachie virus, mumps virus, measles virus, rubella virus, polio virus, human immunodeficiency virus type I (HIV-I), and human immunodeficiency virus type II (HIV-II).

Bacterial diseases that can be treated or prevented by the methods of the present invention are caused by bacteria including, but not limited to, mycobacteria rickettsia, mycoplasma, neisseria and legionella.

Protozoal diseases that can be treated or prevented by the methods of the present invention are caused by protozoa including, but not limited to, leishmania, kokzidioa, and trypanosoma.

Parasitic diseases that can be treated or prevented by the methods of the present invention are caused by parasites including, but not limited to, chlamydia and rickettsia.

5.7. Target Cancers

Cancers that can be treated or prevented by the methods of the present invention include, but not limited to human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenström's macroglobulinemia, and heavy chain disease. Specific examples of such cancers are described in the sections below.

In a specific embodiment the cancer is metastatic. In another embodiment, the cancer is a tumor. In another specific embodiment, the patient having a cancer is immunosuppressed by reason of having undergone anti-cancer therapy (e.g., chemotherapy radiation) prior to administration of the hsp-sensitized APC.

5.7.1. Colorectal Cancer Metastatic to the Liver

In 1992, approximately 150,000 Americans were diagnosed with colorectal cancer and more than 60,000 died as a result of colorectal metastases. At the time of their deaths, 80 percent of patients with colorectal cancer have metastatic disease involving the liver, and one-half of these patients have no evidence of other (extrahepatic) metastases. Most metastatic tumors of the liver are from gastrointestinal primaries. Unfortunately, the natural history of metastatic liver lesions carries a grave prognosis and systemic chemotherapy regimens have been unable to induce significant response rates or alter length of survival (Drebin, J. A., et al., in *Current Therapy In Oncology*, ed. J. E. Niederhuber, B. C. Decker, Mosby, 1993, p.426).

Colorectal cancer initially spreads to regional lymph nodes and then through the portal venous circulation to the liver, which represents the most common visceral site of metastasis. The symptoms that lead patients with colorectal cancer to seek medical care vary with the anatomical location of the lesion. For example, lesions in the ascending colon frequently ulcerate, which leads to chronic blood loss in the stool.

Radical resection offers the greatest potential for cure in patients with invasive colorectal cancer. Before surgery, the CEA titer is determined. Radiation therapy and chemotherapy are used in patients with advanced colorectal cancer. Results with chemotherapeutic agents (e.g., 5-fluorouracil) are mixed and fewer than 25 percent of patients experience a greater than 50 percent reduction in tumor mass (Richards, 2d., F., et al., 1986, *J. clin. Oncol.* 4:565).

Patients with widespread metastases have limited survival and systemic chemotherapy has little impact in this group of patients. In addition, systemically administered chemotherapy is often limited by the severity of toxicities associated with the various agents, such as severe diarrhea, mucositis and/or myelosuppression. Other techniques, including hepatic radiation, systemic chemotherapy, hepatic arterial ligation, tumor embolization and immunotherapy have all been explored, but, for the most part, have proven ineffectual in prolonging patient survival.

In a specific embodiment, the present invention provides compositions and methods for enhancing tumor specific immunity in individuals suffering from colorectal cancer metastasized to the liver, in order to inhibit the progression of the neoplastic disease. Preferred methods of treating these neoplastic diseases comprise administering a composition of autologous macrophage that have been stimulated with hsp noncovalently bound to peptide complexes, which elicits tumor-specific immunity against the tumor cells. In a specific embodiment, the hsp-stimulated APC of the invention are used to inhibit liver cancer growth in cancer patients, without inducing toxicity.

Accordingly, as an example of the method of the invention, hsp-stimulated APC are administered to a patient diagnosed with colorectal cancer, with or without liver metastasis, by intravenous injection.

5.7.2. Hepatocellular Carcinoma

Hepatocellular carcinoma is generally a disease of the elderly in the United States. Although many factors may lead to hepatocellular carcinoma, the disease is usually limited to those persons with preexisting liver disease. Approximately 60 to 80 percent of patients in the United States with hepatocellular carcinoma have a cirrhotic liver and about four percent of individuals with a cirrhotic liver eventually develop hepatocellular carcinoma (Niederhuber, J. E., (ed.), 1993, *Current Therapy in Oncology*, B. C. Decker, Mosby). The risk is highest in patients whose liver disease is caused by inherited hemochromatosis or hepatitis B viral infection (Bradbear, R. A., et al., 1985, *J. Natl. Cancer Inst.* 75:81; Beasley, R. P., et al., 1981, *Lancet* 2:1129). Other causes of cirrhosis that can lead to hepatocellular carcinoma include alcohol abuse and hepatic fibrosis caused by chronic administration of methotrexate. The most frequent symptoms of hepatocellular carcinoma are the development of a painful mass in the right upper quadrant or epigastrium, accompanied by weight loss. In patients with cirrhosis, the development of hepatocellular carcinoma is preceded by ascites, portal hypertension and relatively abrupt clinical deterioration. In most cases, abnormal values in standard liver function tests such as serum aminotransferase and alkaline phosphatase are observed.

CT scans of the liver are used to determine the anatomic distribution of hepatocellular carcinoma and also provide orientation for percutaneous needle biopsy. Approximately 70 percent of patients with hepatocellular carcinoma have an elevated serum alpha-fetoprotein concentration (McIntire, K. R., et al., 1975, *Cancer Res.* 35:991) and its concentration correlates with the extent of the disease.

Radical resection offers the only hope for cure in patients with hepatocellular carcinoma. Such operative procedures are associated with five-year survival rates of 12 to 30 percent. Liver transplantation may improve survival of some younger individuals. However, most patients are not surgical candidates because of extensive cirrhosis multifocal tumor pattern or scarcity of compatible donor organs. Chemotherapeutic agents have been administered either by intravenous route or through an intrahepatic arterial catheter. Such therapy has sometimes been combined with irradiation to the liver. Reductions in the size of measurable tumors of 50% or more have been reported in some patients treated with either systemic doxorubicin or 5-fluorouracil. However, chemotherapy often induces immunosuppression and rarely causes the tumor to disappear completely and the duration of response is short. The prognosis for patients with hepatocellular carcinoma is negatively correlated with cirrhosis and metastases to the lungs or bone. Median survival for patients is only four to six months. In another specific embodiment, the present invention provides compositions and methods for enhancing specific immunity in individuals suffering from hepatocellular carcinoma in order to inhibit the progression of the neoplastic disease and ultimately eliminate all preneoplastic and neoplastic cells.

5.7.3. Breast Cancer

Another specific aspect of the invention relates to the treatment of breast cancer. The American Cancer Society estimated that in 1992 180,000 American women were diagnosed with breast cancer and 46,000 succumbed to the disease (Niederhuber, J. E. ed. *Current Therapy in Oncology* B. C. Decker, Mosby, 1993). This makes breast cancer the second major cause of cancer death in women, ranking just behind lung cancer. A disturbing fact is the observation that breast cancer has been increasing at a rate of 3 percent per year since 1980 (Niederhuber, J. E., ed. *Current Therapy in Oncolopy*, B. C. Decker, Mosby, (1993)). The treatment of breast cancer presently involves surgery, radiation, hormonal therapy and/or chemotherapy. Consideration of two breast cancer characteristics, hormone receptors and disease extent, has governed how hormonal therapies and standard-dose chemotherapy are sequenced to improve survival and maintain or improve quality of life. A wide range of multi-drug regimens have been used as adjuvant therapy in breast cancer patients, including, but not limited to combinations of 2 cyclophosphamide, doxorubicin, vincristine methotrexate, 5-fluorouracil and/or leucovorin. In a specific embodiment, the present invention provides hsp compositions and methods for enhancing specific immunity to preneoplastic and neoplastic mammary cells in women. The present invention also provides compositions and methods for preventing the development of neoplastic cells in women at enhanced risk for breast cancer, and for inhibiting cancer cell proliferation and metastasis. These compositions can be applied alone or in combination with each other or with biological response modifiers.

5.8. Autologous Embodiment

In a preferred embodiment of the invention directed to the use of autologous APC stimulated with autologous complexes of hsp-peptides for the treatment or prevention of cancer, two of the most intractable hurdles to cancer immunotherapy are circumvented. First is the possibility that human cancers, like cancers of experimental animals, are antigenically distinct. In a preferred embodiment of the present invention, hsps chaperone antigenic peptides of the cancer cells from which they are derived and circumvent this hurdle. Second, most current approaches to cancer immunotherapy focus on determining the CTL-recognized epitopes of cancer cell lines. This approach requires the availability of cell lines and CTLs against cancers. These reagents are unavailable for an overwhelming proportion of human cancers. In an embodiment of the present invention directed to the use of autologous macrophages stimulated with autologous complexes comprising hsps and peptides, cancer immunotherapy does not depend on the availability of cell lines or CTLs nor does it require definition of the antigenic epitopes of cancer cells. These advantages make autologous hsp-stimulated APC attractive and novel immunogens against cancer.

5.9. Prevention and Treatment of Primary and Metastatic Neoplastic Diseases

There are many reasons why immunotherapy as provided by the present invention is desired for use in cancer patients. First, if cancer patients are immunosuppressed and surgery, with anesthesia, and subsequent chemotherapy, may worsen the immunosuppression, then with appropriate immunotherapy in the preoperative period, this immunosuppression may be prevented or reversed. This could lead to fewer infectious complications and to accelerated wound healing. Second, tumor bulk is minimal following surgery and immunotherapy is most likely to be effective in this situation. A third reason is the possibility that tumor cells are shed into the circulation at surgery and effective immunotherapy applied at this time can eliminate these cells.

In a specific embodiment, the preventive and therapeutic methods of the invention are directed at enhancing the immunocompetence of the cancer patient either before surgery, at or after surgery, and to induce tumor-specific immunity to cancer cells, with the objective being inhibition of cancer, and with the ultimate clinical objective being total cancer regression and eradication.

5.10. Monitoring of Effects After Adoptive Immunotherapy

The effect of immunotherapy with hsp-stimulated APC on development and progression of neoplastic diseases can be monitored by any methods known to one skilled in the art, including but not limited to measuring: a) delayed hypersensitivity as an assessment of cellular immunity; b) activity of cytolytic T-lymphocytes in vitro; c) levels of tumor specific antigens, e.g., carcinoembryonic (CEA) antigens; d) changes in the morphology of tumors using techniques such as a computed tomographic (CT) scan; e) changes in levels of putative biomarkers of risk for a particular cancer in individuals at high risk; and f) changes in the morphology of tumors using a sonogram.

5.10.1. Delayed Hypersensitivity Skin Test

Delayed hypersensitivity skin tests are of great value in the overall immunocompetence and cellular immunity to an antigen. Inability to react to a battery of common skin antigens is termed anergy (Sato, T., et al, 1995, *Clin. Immunol. Pathol.* 74:35–43).

Proper technique of skin testing requires that the antigens be stored sterile at 4° C., protected from light and reconstituted shortly before use. A 25- or 27-gauge needle ensures intradermal, rather than subcutaneous, administration of antigen. Twenty-four and 48 hours after intradermal administration of the antigen, the largest dimensions of both erythema and induration are measured with a ruler. Hypoactivity to any given antigen or group of antigens is confirmed by testing with higher concentrations of antigen or, in ambiguous circumstances, by a repeat concentration with an intermediate test.

5.10.2. Activity of Cytolytic T-lymphocytes In Vitro

Eight$\times 10^6$ peripheral blood derived T lymphocytes isolated by the Ficoll-Hypaque centrifugation gradient technique, are restimulated with $4\times 10^4$ mitomycin C treated tumor cells in 3 ml RPMI medium containing 10% fetal calf serum. In some experiments, 33% secondary mixed lymphocyte culture supernatant or IL-2, is included in the culture medium as a source of T cell growth factors.

In order to measure the primary response of cytolytic T-lymphocytes after immunization, T cells are cultured without the stimulator tumor cells. In other experiments, T cells are restimulated with antigenically distinct cells. After six days, the cultures are tested for cytotoxity in a 4 hour $^{51}$Cr-release assay. The spontaneous $^{51}$Cr-release of the targets should reach a level less than 20%. For the anti-MHC class I blocking activity, a tenfold concentrated supernatant of W6/32 hybridoma is added to the test at a final concentration of 12.5% (Heike M., et al., *J. Immunotherapy* 15:165–174).

5.10.3. Levels of Tumor Specific Antigens

Although it may not be possible to detect unique tumor antigens on all tumors, many tumors display antigens that distinguish them from normal cells. The monoclonal antibody reagents have permitted the isolation and biochemical characterization of the antigens and have been invaluable diagnostically for distinction of transformed from nontransformed cells and for definition of the cell lineage of transformed cells. The best-characterized human tumor-associated antigens are the oncofetal antigens. These antigens are expressed during embryogenesis, but are absent or very difficult to detect in normal adult tissue. The prototype antigen is carcinoembryonic antigen (CEA), a glycoprotein found on fetal gut an human colon cancer cells, but not on normal adult colon cells. Since CEA is shed from colon carcinoma cells and found in the serum, it was originally thought that the presence of this antigen in the serum could be used to screen patients for colon cancer. However, patients with other tumors, such as pancreatic and breast cancer, also have elevated serum levels of CEA. Therefore, monitoring the fall and rise of CEA levels in cancer patients undergoing therapy has proven useful for predicting tumor progression and responses to treatment.

Several other oncofetal antigens have been useful for diagnosing and monitoring human tumors, e.g., alpha-fetoprotein, an alpha-globulin normally secreted by fetal liver and yolk sac cells, is found in the serum of patients with liver and germinal cell tumors and can be used as a matter of disease status.

5.10.4. Computed Tomographic (CT) Scan

CT remains the choice of techniques for the accurate staging of cancers. CT has proved more sensitive and specific than any other imaging techniques for the detection of metastases.

5.10.5. Measurement of Putative Biomarkers

The levels of a putative biomarker for risk of a specific cancer are measured to monitor the effect of hsp noncovalently bound to peptide complexes. For example, in individuals at enhanced risk for prostate cancer, serum prostate-specific antigen (PSA) is measured by the procedure described by Brawer, M. K., et. al., 1992, *J. Urol.* 147:841–845, and Catalona, W. J., et al., 1993, *JAMA* 270:948–958; or in individuals at risk for colorectal cancer CEA is measured as described above in Section 4.5.3; and in individuals at enhanced risk for breast cancer, 16-α-hydroxylation of estradiol is measured by the procedure described by Schneider, J. et al., 1982, *Proc. Natl. Acad. Sci. USA* 79:3047–3051. The references cited above are incorporated by reference herein in their entirety.

5.10.6. Sonogram

A Sonogram remains an alternative choice of technique for the accurate staging of cancers.

6. EXAMPLES

EXOGENOUS HEAT SHOCK PROTEIN-ASSOCIATED PEPTIDES ARE RE-PRESENTED BY MHC I MOLECULES OF MACROPHAGE

The possibility of re-presentation of HSP-chaperoned peptides by phagocytic cells was tested directly using a vesicular stomatitis virus (VSV) model, for example, the VSV-infected cell line, EL4 cells.

6.1. Methods and Materials

Gp96 was isolated to apparent homogeneity from EL4 cells transfected with the gene encoding the nucleocapsid protein of VS1 (N1 cells) and from untransfected EL4 cells (negative control), according to procedures described above in Section 5.

Macrophages were prepared from 0.2 ml pristane-induced peritoneal exudate cells from C57BL/6 mice.

6.2. Ability of Sensitized Macrophages to Stimulate TNF Release by CTLS $1 \times 10^4$ macrophages were cultured in the presence of gp96 (2 or 10 microgram/ml derived from N1 cells or EL4 cells) and VSV peptide-specific CTL ($5 \times 10^4$) in 96-well U-bottom plate at 37° C. After 24 hr supernatants were collected and TNF-α product was measured by bioassay in a cytotoxicity assay using WEHI164 cells.

WEHI164 cells ($2.5 \times 10^2$/well) were cocultured with serially diluted supernatants obtained previously as described above. TNF-α was cultured with WEHI164 cells in separate wells as control. After a 4 hr incubation at 37° C., 50 μl 3-[4,5-dimethyl thiazol-2-yl]-2,5-dipheyl tetrazolium bromide (MTT) (SIGMA, St. Louis) (1 mg/ml) was added and incubated for a further 4 hr. 100 microliter of propanol-0.05M HCl was added and the optic density was measured immediately at 590 nm. Sample concentrations were calculated by comparison with dilution points which resulted in killing of 50% of WEHI164 cells.

6.2.1. Results

Macrophages sensitized with gp96 isolated from N1 cells stimulated release of TNF by VSV-specific CTLs, while those sensitized with gp96 isolated from EL4 cells did not (FIG. 1A).

6.3. Ability of Sensitized Macrophages to Act As Targets of CTLs

Peritoneal macrophages ($5 \times 10^6$) were sensitized with gp96 (10 micrograms/ml) derived from N1 cells, EL4 cells, VSV nucleocapsid $K^b$ epitope peptide (10 micro M) as a positive control, or culture medium as control, for 2 hr at 37° C., followed by labeling with $^{51}$Cr for 1.5 hr. These sensitized macrophages were used as targets in a 4 hr $^{51}$Cr-release assay with VSV-specific CTLs.

Anti-CD4 mAb (CK1.5), anti-CD8 mAb (YTS169.4), anti-H-2$K^b$ mAb (Y3), anti-H-2$D^b$ mAb (B22.249) or RPMI control were added to the CTL assay at the same time as effector cells and $^{51}$Cr-labeled macrophages sensitized with gp96 from N1 cells.

6.3.1. Results

Macrophages sensitized with gp96 isolated from N1 cells were lysed by anti-VSV CTLs whereas those sensitized with gp96 from EL4 cells were not (FIG. 1B). The lysis is blocked by anti-MHC class I (Jb) and anti-CD8 antibodies but not by anti-MHC class I (D6) and anti-CD4 antibodies (FIG. 1C).

Thus, gp96 molecules isolated from N1 cells chaperone the $K^b$-epitope of VSV and this epitope is inducted into the endogenous presentation pathway of macrophages.

7. EXAMPLES

ADOPTIVE TRANSFER OF SENSITIZED MACROPHAGES

7.1. Materials and Methods

Peritoneal macrophages were collected three days after injecting nominally healthy BALB/cJ mice with 0.2 ml pristane (Sigma, St. Louis) intraperitoneally, by centrifuging the peritoneal exudate.

Peritoneal exudate cells (PEC) or macrophages ($4 \times 10^7$) were incubated at 37° C. for 3 hr in 1 ml RPMI containing 50 μg gp96-peptide complexes derived from Methylcholanthrene-induced tumors or from liver. The macrophages were then washed 3 times and resuspended at a concentrate of $1 \times 10^7$/ml in RPMI medium. 200 microliter of this suspension was used to inject mice intraperitoneally as described in the experimental protocol below.

7.2. Methylcholanthrene (Meth A)-Induced Sarcoma Model

Five groups of mice were given the following treatments: a) Subcutaneous injection of buffer solution; b) Subcutaneous injection of 9 μg gp96-peptide complexes derived from liver tissue; c) Intraperitoneal injection with $5 \times 10^6$ PEC or macrophages sensitized with gp96-peptide complexes derived from normal liver; d) Subcutaneous injection containing 9 μg gp96-peptide complexes derived from Meth A tumor cells; and e) Intraperitoneal injection with $5 \times 10^6$ PEC or macrophages sensitized with gp96 peptide complexes derived from Meth A tumor cells.

The above treatment regimes were administered twice, at weekly intervals before injecting intradermally, 1 week after the second injection, $1 \times 10^5$ Meth A tumor cells. Tumor growth was monitored by measuring the average tumor diameter.

7.3. Results

Tumor growth was comparable in groups A, B and C, i.e. mice receiving the control buffer solution or the gp96 derived from liver tissue. In mice treated directly with gp96-peptide complexes (D) or with gp96-peptide complex sensitized macrophages, (E) tumor growth was markedly inhibited compared with the mice receiving the buffer control or the gp96 derived from liver FIGS. 2A–2E. Thus, administration of gp96-peptide complexes directly or adoptive therapy with macrophages and/or other APC sensitized with gp96-peptide complexes, described herein, represents an approach to treatment of cancer with potential applicability to a wide range of cancers, infectious diseases or immunological disorders.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of treating an individual having a type of cancer or metastasis comprising the steps of:
    (a) sensitizing antigen presenting cells in vitro with a sensitizing-effective amount of a purified complex of a heat shock protein noncovalently bound to an antigenic molecule, wherein said complex is obtained from or, said antigenic molecule is immunospecific to said type of cancer or metastasis; and
    (b) administering to an individual having said type of cancer or metastasis a therapeutically effective amount of the sensitized antigen presenting cells.

2. A method of treating an individual having a type of cancer or metastasis comprising administering to the individual a therapeutically effective amount of sensitized antigen presenting cells, in which the antigen presenting cells have been sensitized in vitro with a purified complex of a heat shock protein noncovalently bound to an antigenic molecule, wherein said complex is obtained from or, said antigenic molecule is immunospecific to said type of cancer or metastasis.

3. The method according to claim 1 wherein the individual is human.

4. The method according to claim 2 wherein the individual is human.

5. The method according to claim 3 wherein the antigen presenting cells are autologous to the human.

6. The method according to claim 4 wherein the antigen presenting cells are autologous to the human.

7. The method according to claim 3 wherein the antigen presenting cells are allogeneic to the human.

8. The method according to claim 4 wherein the antigen presenting cells are allogeneic to the human.

9. The method according to claim 3 or 4 wherein the cancer is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, multiple myeloma, Waldenström's macroglobulinemia, and heavy chain disease.

10. The method according to claim 3 or 4 wherein the heat shock protein is selected from the group consisting of hsp70, hsp90, gp96, and a combination thereof.

11. The method according to claim 4 wherein the heat shock protein is hsp70.

12. The method of according to claim 4 wherein the heat shock protein is hsp90.

13. The method according to claim 4 wherein the heat shock protein is gp96.

14. The method according to claim 4 wherein the complex is isolated from a cancer or metastasis autologous to the human.

15. The method according to claim 4 wherein the complex is isolated from a cancer or metastasis allogeneic to the human.

16. The method according to claim 4 further comprising administering to the human an effective amount of a biological response modifier selected from the group consisting of interferon-$\alpha$, interferon-$\gamma$, interleukin-2, interleukin-4, interleukin-6 and tumor necrosis factor.

17. The method according to claim 4 wherein the therapeutically effective amount is in the range of $10^6$ to $10^{12}$ cells.

18. The method according to claim 4 wherein the cells are administered intravenously.

19. The method according to claim 4 wherein the antigenic molecule is an exogenous antigenic molecule.

20. The method according to claim 19 in which the exogenous antigenic molecule is a tumor antigen.

21. A pharmaceutical composition comprising a therapeutically effective amount of sensitized antigen presenting cells, in a pharmaceutically acceptable carrier, in which the antigen presenting cells have been sensitized in vitro with a purified complex of a heat shock protein noncovalently bound to an antigenic molecule, wherein said complex is obtained from or, said antigenic molecule is immunospecific to a type of cancer or metastasis.

22. The composition of claim 21 in which the antigen presenting cells are human.

23. The composition of claim 22 wherein the heat shock protein is selected from the group consisting of hsp70, hsp90, gp96 and a combination thereof.

24. A method of inhibiting growth of a type of cancer or metastasis in an individual in whom such inhibition is desired comprising the steps of:
  (a) sensitizing antigen presenting cells in vitro with a sensitizing-effective amount of a purified complex of a heat shock protein noncovalently bound to an antigenic molecule, wherein said complex is obtained from or, said antigenic molecule is immunospecific to said type of cancer or metastasis; and
  (b) administering a therapeutically effective amount of the sensitized antigen presenting cells to an individual in whom inhibition of growth of said type of cancer or metastasis is desired.

25. A method of inhibiting growth of a type of cancer or metastasis in an individual in whom such inhibition is desired comprising administering to the individual a therapeutically effective amount of sensitized antigen presenting cells, in which the antigen presenting cells have been sensitized in vitro with a purified complex of a heat shock protein noncovalently bound to an antigenic molecule, wherein said complex is obtained from or, said antigenic molecule is immunospecific to said type of cancer or metastasis.

26. The method according to claim 3, 4, 6 or 25 in which the antigen presenting cells are macrophages.

27. The composition of claim 21 or 22 in which the antigen presenting cells are purified.

28. The method according to claim 1 in which the antigen presenting cells that are administered to the individual are purified.

29. The method of claim 24 or 25 in which the sensitized antigen presenting cells are administered to the individual after said type of cancer or metastasis in the individual had been removed by surgery.

* * * * *